US00PP26495P2

(12) United States Plant Patent
Koning

(10) Patent No.: US PP26,495 P2
(45) Date of Patent: Mar. 8, 2016

(54) ***LAVANDULA* PLANT NAMED 'ANOUK DELUXE 901'**

(50) Latin Name: *Lavandula stoechas*
Varietal Denomination: Anouk Deluxe 901

(71) Applicant: Lammert Koning, Nuis (NL)

(72) Inventor: Lammert Koning, Nuis (NL)

(73) Assignee: New Variety B.V., Kudelstaart (NL)

( * ) Notice: Subject to any disclaimer, the term of this patent is extended or adjusted under 35 U.S.C. 154(b) by 126 days.

(21) Appl. No.: 14/120,162

(22) Filed: Apr. 30, 2014

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'Anouk Deluxe 901', characterized by its compact and somewhat upright plant habit; freely branching growth habit; dense and bushy appearance; durable narrow leaves; freely flowering habit; light violet blue and dark purple-colored flowers positioned on strong and erect peduncles; and good garden performance.

1 Drawing Sheet

Botanical designation: *Lavandula stoechas.*
Cultivar denomination: 'ANOUK DELUXE 901'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 901'.

The new Lavender plant is a product of a planned breeding program conducted by the Inventor in Nuis, The Netherlands. The objective of the breeding program was to develop new strong *Lavandula* plants with attractive plant form and flower coloration.

The new *Lavandula* plant originated from a cross-pollination made by the Inventor in August, 2006 of *Lavandula stoechas* 'Anouk', disclosed in U.S. Plant Pat. No. 16,685, as the female, or seed, parent with a proprietary selection of *Lavandula stoechas* identified as code number L.722, not patented, as the male, or pollen, parent. The new *Lavandula* plant was discovered and selected by the Inventor during 2008 as a single flowering plant within the progeny of the stated cross-pollination in a controlled environment in Nuis, The Netherlands.

Asexual reproduction of the new *Lavandula* plant by terminal cuttings in a controlled greenhouse environment in De Lier, The Netherlands since September, 2009 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 901' as a new and distinct *Lavandula* plant:

1. Compact and somewhat upright plant habit.
2. Freely branching growth habit; dense and bushy appearance.
3. Durable narrow leaves.
4. Freely flowering habit.
5. Light violet blue and dark purple-colored flowers positioned on strong and erect peduncles.
6. Good garden performance.

Plants of the new *Lavandula* differ from plants of the female parent, 'Anouk', primarily in plant habit as plants of the new *Lavandula* are more compact and bushier than plants of 'Anouk'.

Plants of the new *Lavandula* differ from plants of the male parent selection primarily in peduncle length as peduncles of plants of the new *Lavandula* are shorter than peduncles of plants of the male parent selection.

Plants of the new *Lavandula* can be compared to plants of the *Lavandula stoechas* 'Silver Anouk', disclosed in U.S. Plant Pat. No. 20,068. In side-by-side comparisons, plants of the new *Lavandula* differ from plants of 'Silver Anouk' in the following characteristics:

1. Plants of the new *Lavandula* are more compact and bushier than plants of 'Silver Anouk'.
2. Plants of the new *Lavandula* and 'Silver Anouk' differ in leaf color.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph comprises a side perspective view of a typical flowering plant of 'Anouk Deluxe 901' grown in a container.

DETAILED BOTANICAL DESCRIPTION

Plants used in the aforementioned photograph and following detailed description were grown in 12-cm containers during the early summer in a glass-covered greenhouse in Boskoop, The Netherlands and under cultural practices typical of commercial *Lavandula* production. Plants were pinched two times and were ten months old when the photograph and description were taken. During the production of the plants, day temperatures ranged from 14° C. to 26° C. and night temperatures ranged from 6° C. to 18° C. In the following description, color references are made to The Royal Horticultural Society Colour Chart, 2007 Edition, except where general terms of ordinary dictionary significance are used.

Botanical classification: *Lavandula stoechas* 'Anouk Deluxe 901'.

Parentage:

*Female, or seed, parent.*—*Lavandula stoechas* 'Anouk', disclosed in U.S. Plant Pat. No. 16,685.

*Male, or pollen, parent.*—Proprietary selection of *Lavandula stoechas* identified as code number L.722, not patented.

Propagation:

*Type.*—Terminal vegetative cuttings.

*Time to initiate roots, summer.*—About one week at temperatures ranging from 14° C. to 26° C.

*Time to initiate roots, winter.*—About ten days at temperatures ranging from 14° C. to 26° C.

*Time to produce a rooted young plant, summer.*—About three to four weeks at temperatures ranging from 14° C. to 26° C.

*Time to produce a rooted young plant, winter.*—About four to six weeks at temperatures ranging from 14° C. to 26° C.

*Root description.*—Fine, fibrous; white in color.

*Rooting habit.*—Freely branching; dense.

Plant description:

*Plant and growth habit.*—Herbaceous perennial; compact and somewhat upright plant habit; freely branching habit, dense and bushy appearance; moderately vigorous growth habit; flowers arranged in verticillasters on crowded spikes with showy terminal flower bracts.

*Plant height.*—About 26.7 cm.

*Plant width.*—About 19.7 cm.

*Lateral branch description.*—Quantity per plant: About ten. Length, from stem to base of inflorescence: About 12.5 cm. Diameter: About 3 mm. Internode length: About 1.6 cm. Strength: Strong. Aspect: Mostly upright. Texture: Densely tomentose. Color: Close to 143C and 145B; pubescence, close to 157C to 157D.

*Leaf description.*—Arrangement: Opposite, simple; sessile. Length: About 3 cm. Width: About 4.5 mm. Shape: Lanceolate. Apex: Acute. Base: Cuneate. Margin: Entire; very slightly revolute. Texture, upper and lower surfaces: Densely pubescent. Fragrance: Strongly aromatic, pungent. Venation pattern: Pinnate. Color: Developing leaves, upper surface: Between 137C and 191A. Developing leaves, lower surface: Close to 191B. Fully expanded leaves, upper surface: Between 137A and 189A; venation, close to 191B; pubescence, close to 157C to 157D. Fully expanded leaves, lower surface: Between 189A and 191A; venation, close to 191B; pubescence, close to 157C to 157D.

Flower description:

*Flower type, arrangement and habit.*—Small single flowers arranged in compact verticillasters on crowded spikes; freely flowering, about 130 flowers developing per inflorescence; flowers tubular with five lobes; inflorescences with showy terminal bracts.

*Natural flowering season.*—Long flowering period; continuous from late spring into the late summer in The Netherlands.

*Flower longevity on the plant.*—Individual inflorescences last about two weeks on the plant; flowers not persistent.

*Fragrance.*—None detected.

*Flower buds.*—Length: About 7 mm. Diameter: About 2 mm. Shape: Narrowly oblong. Color: Close to 152A; base, close to 144C.

*Inflorescence size.*—Height: About 6.5 cm. Diameter, apex: About 1.5 cm. Diameter, base: About 1.7 cm.

*Flower size.*—Diameter: About 4 mm. Depth (height): About 8 mm.

*Petals.*—Quantity and arrangement: Five, fused into a tube. Length: About 7.5 mm to 8 mm. Width: About 2 mm. Shape: Roughly spatulate; lower 75% fused into a tube. Apex: Rounded. Margin: Entire. Texture, upper and lower surfaces: Smooth, glabrous. Color: When opening, upper and lower surfaces: Close to N92B; tube, close to NN155C. Fully opened, upper and lower surfaces: Close to N92B; tube, close to NN155C; color becoming closer to N92C with development.

*Terminal flower bracts.*—Quantity and arrangement: About eight positioned at inflorescence apex. Length: About 1.3 cm. Width: About 7 mm. Shape: Oblong to oblanceolate. Apex: Broadly acute. Base: Cuneate. Margin: Entire; slightly undulate. Texture, upper and lower surfaces: Smooth, glabrous. Color, upper and lower surfaces: Close to 79C to 79D.

*Flower bracts.*—Quantity and arrangement: Each whorl of five flowers is subtended by a single flower bract. Length: About 6 mm. Width: About 6 mm. Shape: Broadly rhomboidal. Apex: Aristate. Base: Cuneate. Margin: Entire. Texture, upper and lower surfaces: Moderately tomentose. Color, upper surface: Close to 147B; venation, close to N186C and N187B. Color, lower surface: Close to 147A to 147B; venation, close to N186C and N187B.

*Sepals.*—Quantity and arrangement: Five, fused into a campanulate tube. Length: About 6 mm. Width: About 0.75 mm. Shape: Lanceolate. Apex: Acute. Margin: Entire. Texture, upper and lower surfaces: Densely tomentose. Color: When opening and fully opened, upper surface: Close to 145A; towards the base, close to 145C. When opening and fully opened, lower surface: Close to 152A; towards the base, close to 144C.

*Peduncles.*—Length: About 5.4 cm. Diameter: About 2.5 mm. Aspect: Mostly upright. Strength: Strong. Texture: Densely pubescent. Color: Close to 137C; pubescence, close to 157C to 157D.

*Reproductive organs.*—Stamens: Quantity per flower: Four. Filament length: About 0.5 mm. Anther shape:

Reniform. Anther length: About 0.5 mm. Anther color: Close to 167B. Pollen amount: Scarce. Pollen color: Close to 12A. Pistils: Quantity per flower: One. Pistil length: About 3.5 mm. Stigma shape: Club-shaped. Stigma color: Close to N186A. Style length: About 3 mm. Style color: Close to 155C. Ovary color: Close to 143B.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 901' as illustrated and described.

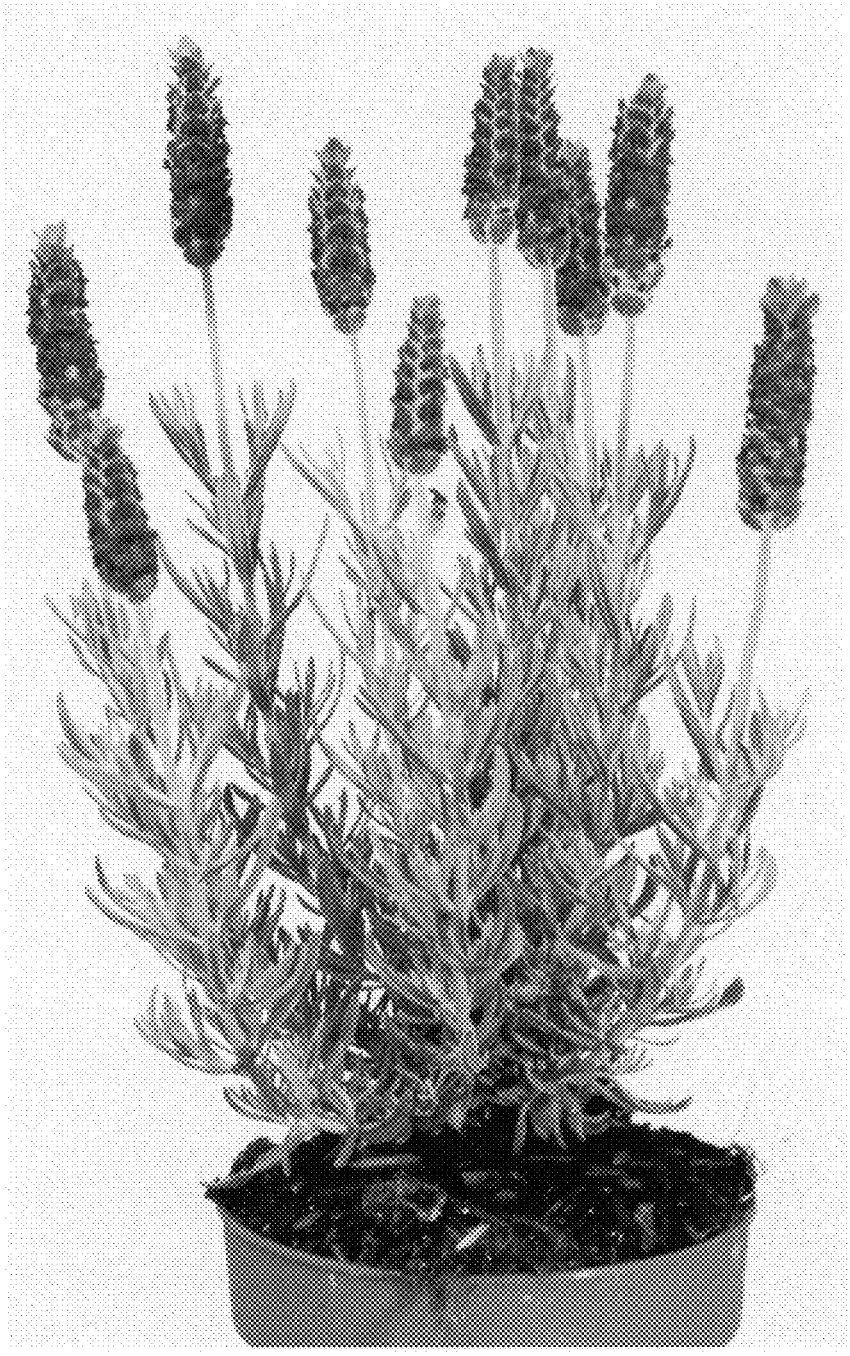

* * * * *